(12) United States Patent
Mori

(10) Patent No.: US 8,182,623 B2
(45) Date of Patent: May 22, 2012

(54) ABSORBENT ARTICLE, ABSORBENT BODY FOR ABSORBENT ARTICLE, AND MANUFATURING PROCESS THEREFOR

(75) Inventor: Koichi Mori, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 182 days.

(21) Appl. No.: 12/725,107

(22) Filed: Mar. 16, 2010

(65) Prior Publication Data

US 2010/0174259 A1 Jul. 8, 2010

Related U.S. Application Data

(62) Division of application No. 10/116,836, filed on Apr. 5, 2002, now abandoned.

(30) Foreign Application Priority Data

Apr. 6, 2001 (JP) ................................. 2001-108263

(51) Int. Cl.
*D04H 1/54* (2012.01)
*D04H 1/70* (2012.01)
*A61F 13/53* (2006.01)

(52) U.S. Cl. ........ 156/62.2; 264/116; 264/118; 264/122

(58) Field of Classification Search ................. 156/62.2, 156/62.4; 264/115, 116, 118, 122
See application file for complete search history.

(56) References Cited

U.S. PATENT DOCUMENTS

| | | | |
|---|---|---|---|
| 2,964,041 A | 12/1960 | Ashton et al. | |
| 4,061,823 A | 12/1977 | McCaskey et al. | |
| 4,100,324 A * | 7/1978 | Anderson et al. | 442/344 |
| 4,758,466 A | 7/1988 | Dabi et al. | |
| 4,813,948 A * | 3/1989 | Insley | 604/366 |
| 4,921,645 A | 5/1990 | Insley | |
| 5,030,229 A | 7/1991 | Yang | |

FOREIGN PATENT DOCUMENTS

| | | |
|---|---|---|
| JP | 64-68565 | 3/1989 |
| JP | 02-074254 | 3/1990 |
| JP | 8-237956 | 9/1996 |

OTHER PUBLICATIONS

Patent Abstracts of Japan, Publication No. 07024003, Jan. 27, 1995.

* cited by examiner

*Primary Examiner* — Michael Tolin
(74) *Attorney, Agent, or Firm* — Lowe, Hauptman, Ham & Berner, LLP

(57) ABSTRACT

An absorbent body for use in an absorbent article includes: fragments of nonwoven fabric including heat-fusible fibers, the heat-fusible fibers being bonded to each other to have three-dimensional structure in advance of formation of the fragments; and hydrophilic fibers. The nonwoven fabric fragments and the hydrophilic fibers are blended.

4 Claims, 3 Drawing Sheets

ABSORBENT ARTICLE, ABSORBENT BODY FOR ABSORBENT ARTICLE, AND MANUFATURING PROCESS THEREFOR

RELATED APPLICATIONS

The present application is a division of U.S. application Ser. No. 10/116,836 filed, Apr. 5, 2002, now abandoned, which is based on and claims priority from, Japanese Application Number 2001-108263, filed Apr. 6, 2001, the disclosures of which are hereby incorporated by reference herein in their entirety.

BACKGROUND OF THE INVENTION

1. Field of the Invention

The present invention relates to an absorbent article such as disposable diaper, pad for diaper, sanitary napkin, pet sheet and the like. More particularly, the present invention relates to an absorbent body to be used in the absorbent article and a manufacturing process therefor.

2. Description of the Related Art

Generally, absorbent articles are constructed to include: a liquid-permeable topsheet; a liquid-impermeable backsheet; and an absorbent body (absorbent core) interposed between the two sheets. In many cases, the absorbent body is composed of absorbent fibers such as pulp and particulates of absorbent polymer. In case of the absorbent body for use in absorbent article, the improvement of compressive recovery (absorbency) and the improvement of shape stability are important challenge.

Japanese Unexamined Patent Publication (Kokai) No. 2-74254 (74254/1990) discloses an absorbent body which contains 10 to 70% by weight of heat-fusible crimped fibers, 10 to 70% by weight of fluff pulp, and 5 to 50% by weight of particulates of absorbent polymer. In this absorbent body, the heat-fusible crimped fibers are fusion-bonded to each other to have three-dimensional network structure, thereby improving the recovery (absorbency) and shape stability of the absorbent body.

However, in the invention disclosed in Japanese Unexamined Patent Publication No. 2-74254, the density of the three-dimensional framework composed of the heat-fusible fibers, the fluff pulp and the particulate absorbent polymer is high, which becomes a factor of interfering with one of basic functions in absorbent body i.e., swelling of the particulate absorbent polymer when body fluid is absorbed by the particulate polymer. In other words, there is a possibility of decreasing absorbency due to insufficient compressive recovery.

In addition, since the heat-fusible crimped fibers are thermally fusion-bonded to each other after the heat-fusible crimped fibers, the fluff pulp and the particulate absorbent polymer are mixed, the fluff pulp (not heat-fusible fibers) and the particulate absorbent polymer become an interfering factor. More specifically, fusion-bonding of the heat-fusible crimped fibers to each other in a condition where the fluff pulp (not heat-fusible fibers) and the particulate absorbent polymer are mixed therewith, requires large calorie. Here, if the processing temperature is simply set at a high level in order to increase the processing speed, the fusion-bonding can be done only in the surface of the absorbent body but not inside the absorbent body. As a result, sufficient shape stability can not be provided, so that the absorbent article may lose its shape after absorption of liquid. On the other hand, even if the heating rate is lowered, there is a problem of remarkable decrease in productivity, as well as it is still difficult to sufficiently heat inside of the absorbent body.

SUMMARY OF THE INVENTION

The present invention has been worked out in view of the shortcoming in the prior art set forth above. It is therefore an object of the present invention to provide an absorbent body for use in an absorbent article, which has superior absorbency due to improved compressive recovery and superior shape stability.

It is another object of the present invention to provide an absorbent article having superior absorbency and superior shape stability.

It is still another object of the present invention to provide a process for readily manufacturing an absorbent body for use in an absorbent article, which has superior absorbency and superior shape stability.

According to a first aspect of the present invention, there is provided an absorbent body for use in an absorbent article, the absorbent body comprising: fragments of nonwoven fabric including heat-fusible fibers, the heat-fusible fibers being bonded to each other to have three-dimensional structure in advance of formation of the fragments; and hydrophilic fibers, the nonwoven fabric fragments and the hydrophilic fibers being blended. In this absorbent body, since the heat-fusible fibers are bonded to each other to have three-dimensional structure in advance of formation of the nonwoven fabric fragments, vacant spaces are formed inside of the absorbent body to improve the recovery after absorption of liquid. As a result, the absorbency is also improved.

Preferably, the nonwoven fabric fragments are thermally bonded to each other after blending of the nonwoven fabric fragments and the hydrophilic fibers. In this case, since the heat-fusible fibers are bonded to each other to have three-dimensional structure in advance of formation of the nonwoven fabric fragments, the nonwoven fabric fragments can be certainly bonded to each other with relatively small calorie, thereby improving the productivity and the shape stability of the absorbent body. That is, the internal structure of the absorbent body is so stable as to maintain its original shape even after absorption of liquid.

Preferably, the nonwoven fabric fragments consist of the heat-fusible fibers. With this, bonding of the nonwoven fabric fragments can be further facilitated.

Preferably, the hydrophilic fibers are absorbent fibers having high water-absorbency. With this, the absorbency of the absorbent body can increase further.

The absorbent body may further contain 5 to 95% by weight of particulates of superabsorbent polymer, and the blending weight ratio of the nonwoven fabric fragments to the hydrophilic fibers may be from 2:8 to 8:2. With the superabsorbent polymer thus contained, the absorbency of the absorbent body can increase further. With the blending weight ratio of the nonwoven fabric fragments to the hydrophilic fibers in the range from 2:8 to 8:2, on the other hand, well-balanced absorbency can be obtained. In detail, if the blending ratio of the nonwoven fabric fragments to the hydrophilic fibers is smaller than 2:8, compressive recovery may possibly decrease to lower absorbency. If the blending ratio is greater than 8:2, on the other hand, absorbency may possibly decrease since the hydrophilic fibers are not sufficiently present.

Preferably, average dimensions of the nonwoven fabric fragments are set within a range of 3 to 25 mm. More preferably, the average dimensions are set within a range of 5 to 15 mm. With this, it becomes possible to maintain surface smoothness of product and to prevent clogging in production line.

According to a second aspect of the present invention, there is provided an absorbent article comprising a liquid-permeable topsheet, a liquid-impermeable backsheet and an absorbent body disposed between the topsheet and the backsheet. The absorbent body comprises: fragments of nonwoven fabric including heat-fusible fibers, the heat-fusible fibers being bonded to each other to have three-dimensional structure in advance of formation of the fragments; and hydrophilic fibers, the nonwoven fabric fragments and the hydrophilic fibers being blended. In this absorbent article, since the heat-fusible fibers contained in the absorbent article are bonded to each other to have three-dimensional structure in advance of formation of the nonwoven fabric fragments, vacant spaces are formed inside of the absorbent body to improve the recovery after absorption of liquid. As a result, the absorbency is also improved in the absorbent article.

Preferably, the nonwoven fabric fragments are thermally bonded to each other after blending of the nonwoven fabric fragments and the hydrophilic fibers. In this case, since the heat-fusible fibers are bonded to each other to have three-dimensional structure in advance of formation of the nonwoven fabric fragments, the nonwoven fabric fragments can be certainly bonded to each other with relatively small calorie, thereby improving the productivity and the shape stability of the absorbent article housing the absorbent body. That is, the internal structure of the absorbent article is so stable as to maintain its original shape even after absorption of liquid.

Preferably, the nonwoven fabric fragments consist of the heat-fusible fibers. With this, bonding of the nonwoven fabric fragments can be further facilitated.

Preferably, the hydrophilic fibers are absorbent fibers having high water-absorbency. With this, the absorbency of the absorbent article can increase further.

The absorbent body may further contain 5 to 95% by weight of particulates of superabsorbent polymer, and the blending weight ratio of the nonwoven fabric fragments to the hydrophilic fibers may be from 2:8 to 8:2. With the superabsorbent polymer thus contained, the absorbency of the absorbent body can increase further. With the blending weight ratio of the nonwoven fabric fragments to the hydrophilic fibers in the range from 2:8 to 8:2, on the other hand, well-balanced absorbency can be obtained. In detail, if the blending ratio of the nonwoven fabric fragments to the hydrophilic fibers is smaller than 2:8, compressive recovery may possibly decrease to lower absorbency. If the blending ratio is greater than 8:2, on the other hand, absorbency may possibly decrease since the hydrophilic fibers are not sufficiently present.

Preferably, average dimensions of the nonwoven fabric fragments are set within a range of 3 to 25 mm. More preferably, the average dimensions are set within a range of 5 to 15 mm. With this, it becomes possible to maintain surface smoothness of product and to prevent clogging in production line.

According to a third aspect of the present invention, there is provided a process for manufacturing an absorbent body for use in an absorbent article, the manufacturing process comprising: forming nonwoven fabric in which constituent fibers are bonded to each other to have three-dimensional structure; breaking the nonwoven fabric into fragments; blending the nonwoven fabric fragments with hydrophilic fibers; and thermally fusion-bonding the nonwoven fabric fragments to each other. In this manufacturing process, the nonwoven fabric fragments, in which the constituent fibers have been bonded to each other to have three-dimensional structure in advance of formation of the fragments, are first prepared, mixed with the hydrophilic fibers, and then thermally bonded to each other. Therefore, the nonwoven fabric fragments can be bonded to each other with relatively small calorie, thereby improving the productivity. In addition, since the constituent fibers of the nonwoven fabric fragments have been bonded to each other to have three-dimensional structure in advance of fusion-bonding of the nonwoven fabric fragments to each other, the nonwoven fabric fragments can be certainly fusion-bonded to each other, thereby improving the shape stability of the absorbent body.

In this manufacturing process, the absorbent body may further contain 5 to 95% by weight of particulates of superabsorbent polymer, and the blending weight ratio of the nonwoven fabric fragments to the hydrophilic fibers may be from 2:8 to 8:2. With the superabsorbent polymer thus contained, the absorbency of the absorbent body can increase further. With the blending weight ratio of the nonwoven fabric fragments to the hydrophilic fibers in the range from 2:8 to 8:2, on the other hand, well-balanced absorbency can be obtained. In detail, if the blending ratio of the nonwoven fabric fragments to the hydrophilic fibers is smaller than 2:8, compressive recovery may possibly decrease to lower absorbency. If the blending ratio is greater than 8:2, on the other hand, absorbency may possibly decrease since the hydrophilic fibers are not sufficiently present.

Preferably, average dimensions of the nonwoven fabric fragments are set within a range of 3 to 25 mm. More preferably, the average dimensions are set within a range of 5 to 15 mm. With this, it becomes possible to maintain surface smoothness of product and to prevent clogging in production line.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention. It should be noted that the absorbent body according to the present invention can be used for various kinds of absorbent article such as disposable diaper, pad for diaper, sanitary napkin, pet sheet, and the like.

Figure 1:
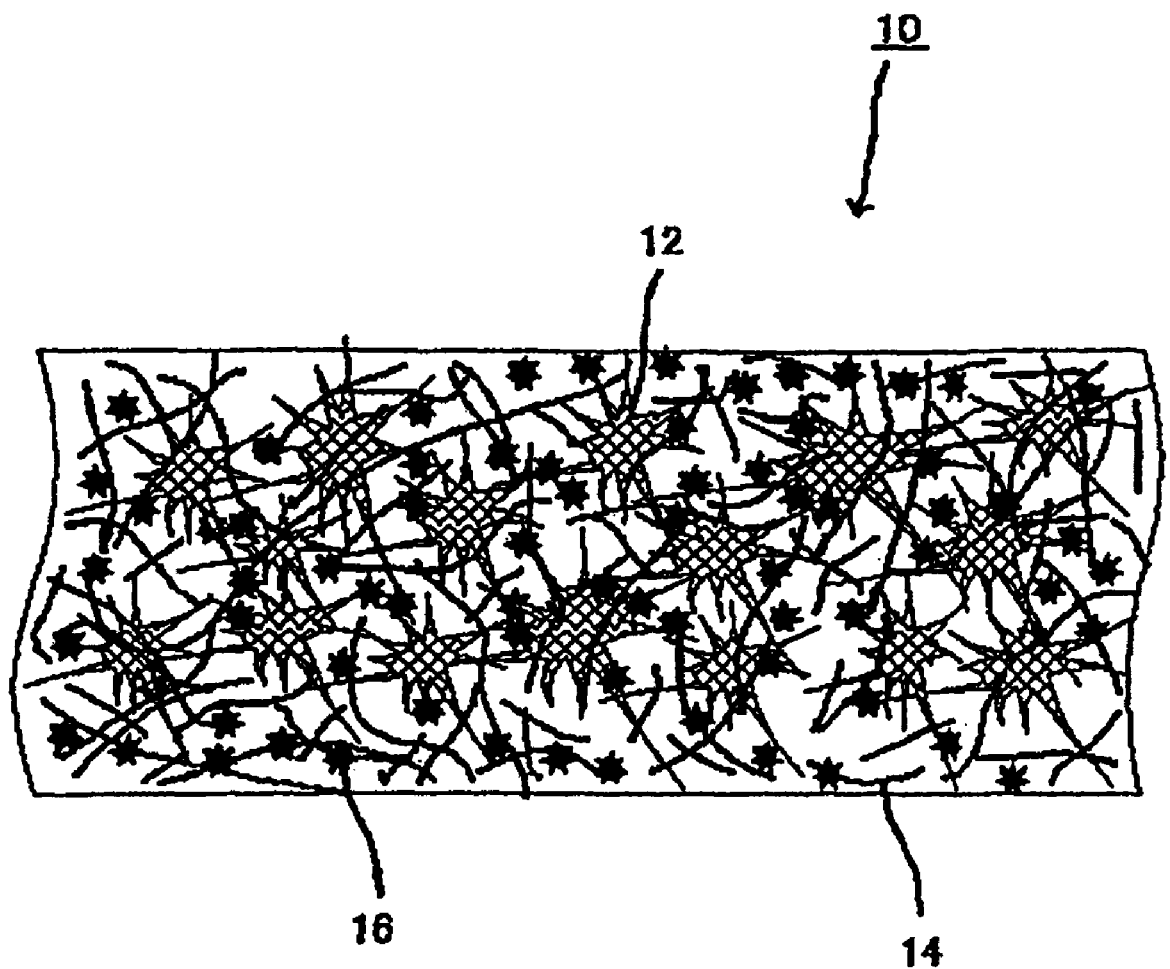
FIG. 1 is an enlarged sectional view, schematically showing a structure of an absorbent body according to one embodiment of the invention.

FIG. 1 shows a structure of an absorbent body 10 according to one embodiment of the present invention. The absorbent body 10 is to be used for an absorbent article. The absorbent body 10 is in sheet form and comprises: fragments 12 formed from nonwoven fabric of which constituent fibers are bonded to each other to have three-dimensional structure in advance of formation of the fragments; hydrophilic fibers 14; and SAP (superabsorbent polymer) 16. The nonwoven fabric fragments 12 mainly contribute to improvement of shape stability of the absorbent body 10. On the other hand, the hydrophilic fibers 14 and the SAP 16 mainly contribute to improvement of liquid absorbency. Here, the nonwoven fabric fragments of three-dimensional structure can be obtained by breaking the nonwoven fabric into small fragments.

For the nonwoven fabric fragments 12, preferably used is thermally bonded nonwoven fabric, such as spunbonded nonwoven fabric, point bonded nonwoven fabric, meltblown nonwoven fabric, through-air bonded nonwoven fabric, or the like. Among them, through-air bonded nonwoven fabric is so bulky, and therefore, it is most preferred in view of compressive recovery. As the constituent fibers forming the nonwoven fabric fragments 12, use can be made of polyolefine fibers, polyester fibers, polyamide fibers, or thick-and-thin type or side-by-side type bicomponent fibers of polyethylene/polypropylene or polyester.

Average dimensions of the nonwoven fabric fragments 12 are preferably set within a range of 3 to 25 mm, more preferably within a range of 3 to 15 mm, for example, to 5 mm. If the average dimensions of the nonwoven fabric fragments 12 are smaller than 3 mm, the compressive recovery is decreased; if greater than 25 mm, the fragments 12 may cause clogging in production line or impair surface smoothness of products. The term "average dimension" as used herein refers to the average of the maximum dimension and the minimum dimension of each fibrous nonwoven fabric fragment. Here, at least 80% of the fibrous nonwoven fabric fragments are preferably set within the foregoing range. That is, it is not necessary to set the average dimensions of all the fragments within the range of 3 to 25 mm. As means for breaking the nonwoven fabric into the fragments 12, cutter mill method or the like can be employed.

As the hydrophilic fibers 14, preferably used are absorbent fibers, such as pulp, cotton, rayon, acetate, or the like. As the SAP (superabsorbent polymer) 16, use can be made of any materials known in the art, for example, such as: sodium polyacrylate; acrylic acid-vinyl alcohol copolymer; sodium polyacrylate crosslinked polymer; (starch-acrylic acid) graft copolymer; (isobutylene-maleic anhydride) copolymer and saponified matter thereof; and polyasparagine acid.

The SAP 16 may be blended into the absorbent body 10, for example, in an amount of 5 to 95% by weight, although it is not necessarily needed for the SAP 16 to be added thereto. On the other hand, the blending ratio of the nonwoven fabric fragments 12 to the hydrophilic fibers 14 based on weight is preferably from 2:8 to 8:2. If the blending ratio is smaller than 2:8, the compressive recovery may possibly decrease to lower the absorbency. If the blending ratio is greater than 8:2, on the other hand, the absorbency may possibly decrease since the hydrophilic fibers are not sufficiently present.

Depending upon applications, the nonwoven fabric fragments 12 are preferably blended in an amount of 20 to 80% by weight. In case of absorbent articles of the type which does not need superior absorbency but regards a pleasant fell to the touch as important, such as panty liners, the amount of the nonwoven fabric fragments 12 is set at 60 to 80%, for example. In case of diapers for bedridden users who are not active but discharge much urine, on the other hand, the amount of the nonwoven fabric fragments 12 is preferably set at 20 to 40%.

It should be noted that when the absorbent body 10 is used for absorbent articles which will be used under a condition where users move relatively vigorously, the nonwoven fabric fragments 12 are thermally bonded to each other. For manufacturing such absorbent body 10, nonwoven fabric in which constituent fibers are bonded to each other to have three-dimensional structure, is first prepared. Then, the nonwoven fabric is broken into the nonwoven fabric fragments 12. The nonwoven fabric fragments 12 are blended with the hydrophilic fibers 14 and the SAP 16. Thereafter, the nonwoven fabric fragments 12 are thermally fusion-bonded to each other. Thus, fusion-bonding of the nonwoven fabric fragments 12 to each other can be performed with relatively small calorie, thereby improving the productivity. In addition, because constituent fibers of each nonwoven fabric fragment 12 have been already bonded to each other to have three-dimensional structure in advance of fusion-bonding of the nonwoven fabric fragments to each other, fusion-bonding of the nonwoven fabric fragments 12 to each other can be certainly performed, thereby improving the shape stability of the absorbent body 10.

Figure 2:
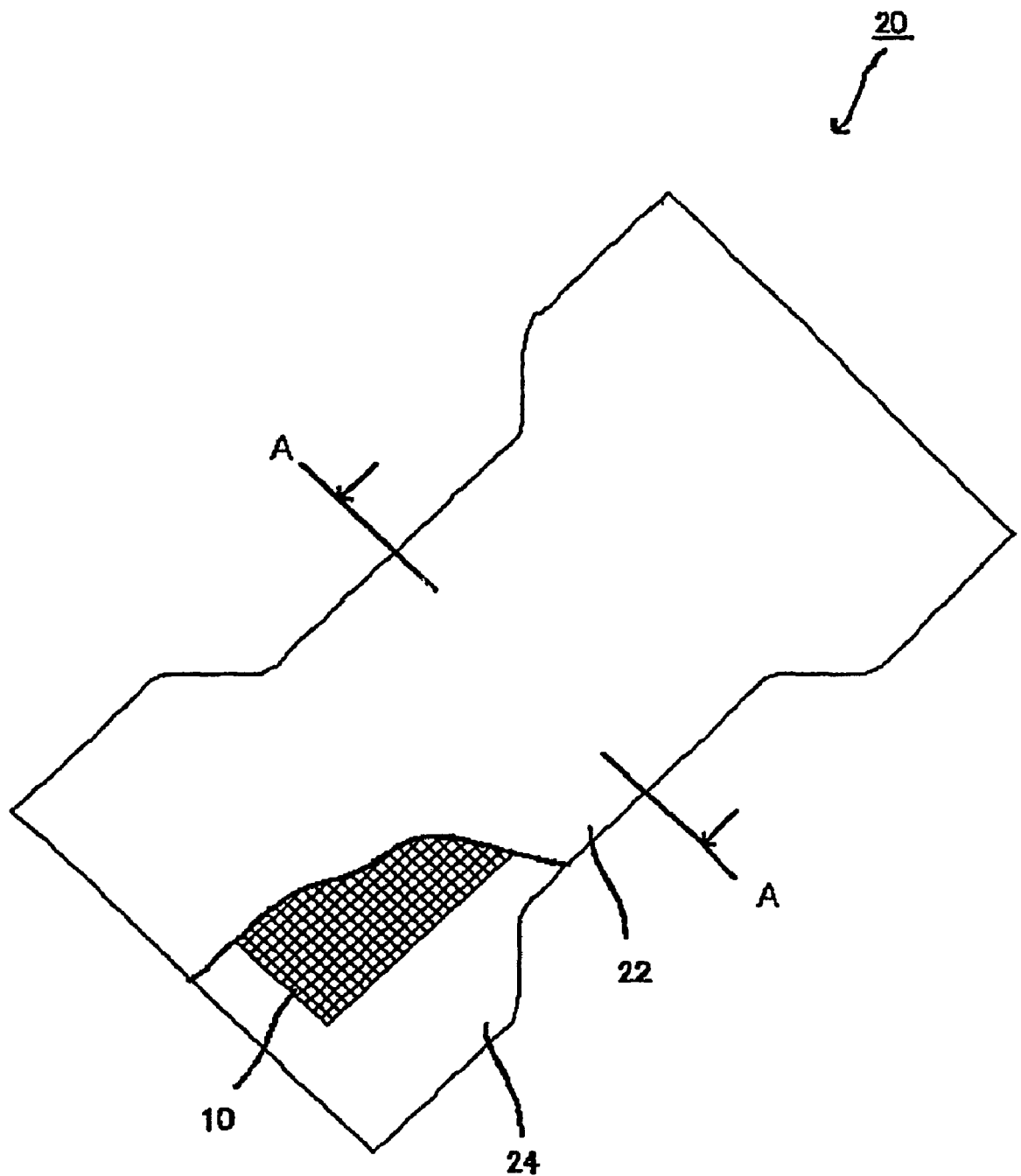
FIG. 2 is a perspective (partially cutaway) view showing a structure of an absorbent article using the absorbent body of FIG. 1.
Figure 3:
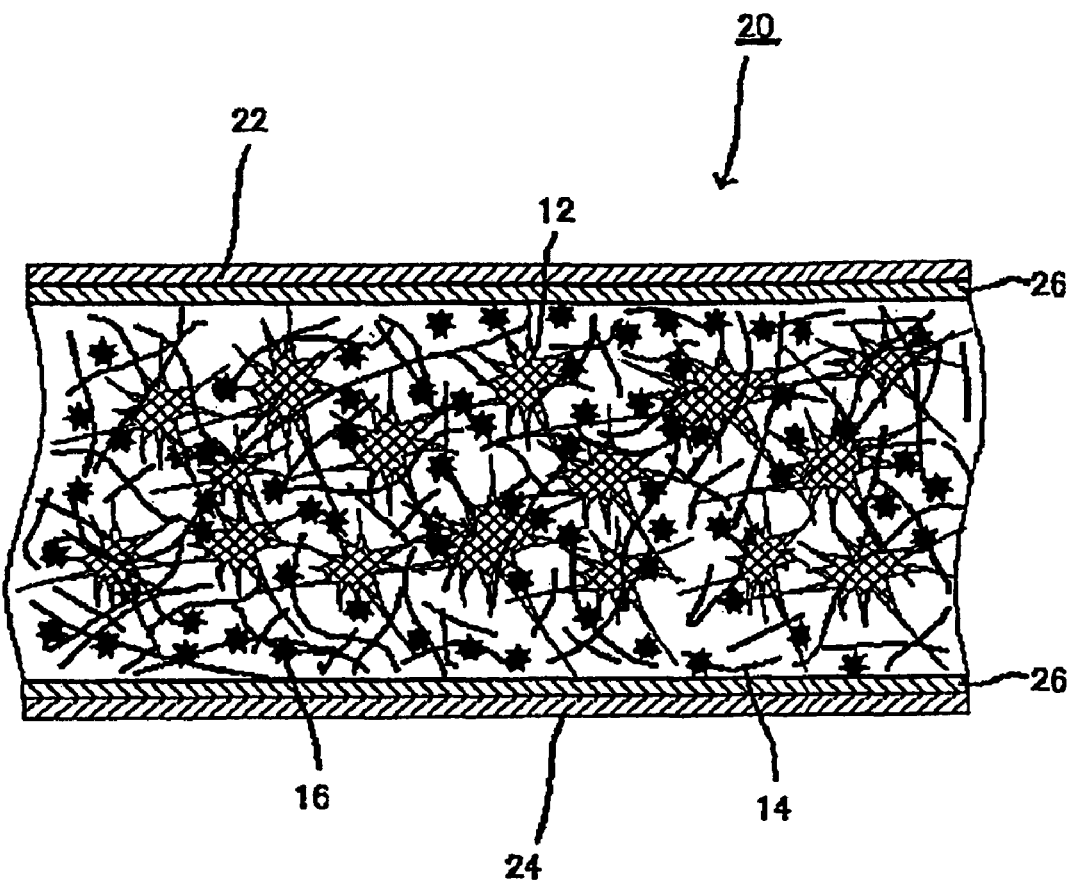
FIG. 3 is a sectional view taken along line A-A of FIG. 2.

FIG. 2 shows an absorbent article 20 using the foregoing absorbent body 10, which is embodied in an open-type disposable diaper. The absorbent article 20 is provided with a liquid-permeable topsheet 22 and a liquid-impermeable backsheet 24. More specifically, as shown in FIG. 3, water-permeable tissue papers 26 are disposed between the topsheet 22 and the absorbent body 10 and between the backsheet 24 and the absorbent body 10. The topsheet 22 and the water-permeable tissue paper 26 opposed to the topsheet 22, and the backsheet 24 and the tissue paper 26 opposed to the backsheet 24 are bonded to each other with a hot-melt adhesive or the like, respectively. Furthermore, the upper and lower tissue papers 26 opposed to the absorbent body may also be bonded to the absorbent body with a hot-melt adhesive or the like. The hot-melt adhesive may be applied in an open pattern selected from patterns of an array of lines, dots, spirals, an array of waves, a lattice and the like. In an alternative, bonding may be directly performed by heat seal, sonic seal or the like.

For the topsheet 22, use can be made of nonwoven fabric formed from hydrophilic fibers; apertured film, or the like. As the hydrophilic fibers, use can be made of thermoplastic fibers (e.g., polyolefine fibers, polyester fibers, polyamide fibers, or thick-and-thin type or side-by-side type bicomponent fibers of polyethylene/polypropylene or polyester) treated to be hydrophilic, or absorbent fibers (e.g., pulp, rayon, acetate or cotton). For the apertured film, preferably used is polyolefine film of polyethylene, polypropylene or the like.

For the backsheet 24, use can be made of polyethylene film, polypropylene film, polyester film, polyurethane film or the like. In case where the absorbent body 10 is used for wearing articles such as disposable diaper, pad, sanitary napkin or the like, the backsheet is preferred to be moisture-permeable.

Even when an external force exerts to deform the absorbent body 10, the absorbent article 20 thus constructed can restore to its original shape after removal of the effect of the external force. In addition, the absorbent article 20 readily conforms to the body shape of the wearer and also exhibits superior follow ability to the body movement. Moreover, the absorbent body 10 exhibits superior absorbency due to the hydrophilic fibers 14 and the SAP 16 blended therein.

As described in detail above with reference to exemplary embodiment thereof, in the absorbent article and the absorbent body used therefor, since the hydrophilic fibers are bonded to each other to have three-dimensional structure in advance of formation of the nonwoven fragments, vacant spaces are formed inside of the absorbent body to improve the recovery after absorption of liquid. As a result, the absorbency is also improved.

In the process for manufacturing the absorbent body, on the other hand, the nonwoven fabric fragments, in which the constituent fibers have been bonded to each other to have three-dimensional structure in advance of formation of the fragments, are first prepared, mixed with the hydrophilic fibers, and then thermally bonded to each other. Therefore, the nonwoven fabric fragments can be bonded to each other with relatively small calorie, thereby improving the productivity. In addition, since the constituent fibers of the nonwoven fabric fragments have been bonded to each other to have three-dimensional structure in advance of fusion-bonding of the nonwoven fabric fragments to each other, the nonwoven fabric fragments can be certainly fusion-bonded to each other, thereby improving the shape stability of the absorbent body.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A process for manufacturing an absorbent body for use in an absorbent article, the manufacturing process comprising:
    forming nonwoven fabric in which constituent fibers are bonded thermally through air to each other to have three-dimensional structure;
    breaking the nonwoven fabric into fragments;
    blending the nonwoven fabric fragments with hydrophilic fibers; and
    thermally fusion-bonding the nonwoven fabric fragments to each other.

2. A manufacturing process as set forth in claim 1, wherein the absorbent body further contains 5 to 95% by weight of particulates of superabsorbent polymer, and the blending weight ratio of the nonwoven fabric fragments to the hydrophilic fibers is from 2:8 to 8:2.

3. A manufacturing process as set forth in claim 1, wherein average dimensions of the nonwoven fabric fragments are set within a range of 3 to 25 mm.

4. A manufacturing process as set forth in claim 3, wherein the average dimensions are set within a range of 5 to 15 mm.

* * * * *